(12) United States Patent
Vitek et al.

(10) Patent No.: US 7,699,780 B2
(45) Date of Patent: Apr. 20, 2010

(54) FOCUSED ULTRASOUND SYSTEM WITH ADAPTIVE ANATOMICAL APERTURE SHAPING

(75) Inventors: Shuki Vitek, Haifa (IL); Kobi Vortman, Haifa (IL)

(73) Assignee: Insightec—Image-Guided Treatment Ltd., Tirat Carmel (IL)

(*) Notice: Subject to any disclaimer, the term of this patent is extended or adjusted under 35 U.S.C. 154(b) by 1000 days.

(21) Appl. No.: 10/916,998

(22) Filed: Aug. 11, 2004

(65) Prior Publication Data

US 2006/0058671 A1 Mar. 16, 2006

(51) Int. Cl.
*A61B 8/00* (2006.01)
*A61N 7/00* (2006.01)
*A61B 5/00* (2006.01)

(52) U.S. Cl. .................................... 600/439; 601/2

(58) Field of Classification Search ................ 600/439, 600/411, 412, 453, 458, 549, 546–545, 407, 600/378–381, 429; 607/27, 89, 96, 115; 601/1–4
See application file for complete search history.

(56) References Cited

U.S. PATENT DOCUMENTS

| | | | |
|---|---|---|---|
| 4,526,168 A * | 7/1985 | Hassler et al. ................ | 601/4 |
| 4,537,074 A * | 8/1985 | Dietz ......................... | 73/625 |
| 4,865,042 A | 9/1989 | Umemura et al. | |
| 4,889,122 A * | 12/1989 | Watmough et al. ............. | 601/3 |
| 5,485,839 A | 1/1996 | Aida et al. | |
| 5,643,179 A | 7/1997 | Fujimoto | |
| 5,665,054 A * | 9/1997 | Dory ......................... | 601/3 |
| 5,722,411 A * | 3/1998 | Suzuki et al. ............... | 600/439 |
| 5,897,495 A * | 4/1999 | Aida et al. .................. | 600/411 |
| 6,267,734 B1 * | 7/2001 | Ishibashi et al. ............. | 601/2 |
| 6,374,132 B1 | 4/2002 | Acker et al. | |
| 6,419,648 B1 | 7/2002 | Vitek et al. | |
| 6,599,256 B1 * | 7/2003 | Acker et al. .................. | 601/2 |
| 6,613,005 B1 | 9/2003 | Friedman et al. | |
| 6,618,620 B1 * | 9/2003 | Freundlich et al. ............ | 607/27 |
| 6,626,855 B1 * | 9/2003 | Weng et al. .................. | 601/3 |
| 6,629,929 B1 * | 10/2003 | Jago et al. ................... | 600/447 |
| 6,790,180 B2 | 9/2004 | Vitek | |

(Continued)

FOREIGN PATENT DOCUMENTS

EP 0 627 206 A2 12/1994

OTHER PUBLICATIONS

PCT International Search Report for PCT/IB2005/002273, Applicant: Insightec—Image Guided Treatment LTD, Forms PCT/ISA/210 and 220, dated Dec. 20, 2005 (6 pages).

(Continued)

*Primary Examiner*—Eric F Winakur
*Assistant Examiner*—Lawrence N Laryea
(74) *Attorney, Agent, or Firm*—Goodwin Procter LLP

(57) ABSTRACT

A method of treating tissue within a body includes directing an ultrasound transducer having a plurality of transducer elements towards target body tissue, and delivering ultrasound energy towards the target tissue from the transducer elements such that an energy intensity at the target tissue is at or above a prescribed treatment level, while an energy intensity at tissue to be protected in the ultrasound energy path of the transducer elements is at or below a prescribed safety level.

22 Claims, 5 Drawing Sheets

U.S. PATENT DOCUMENTS

2002/0082589 A1* 6/2002 Friedman et al. ............. 606/1
2004/0030251 A1* 2/2004 Ebbini et al. ............. 600/443
2004/0068186 A1* 4/2004 Ishida et al. ............. 600/439
2006/0052661 A1* 3/2006 Gannot et al. ............. 600/108

OTHER PUBLICATIONS

PCT Written Opinion of the International Search Authority for PCT/IB2005/002273, Applicant: Insightec—Imange Guided Treatment LTD, Form PCT/ISA/237, dated Dec. 12, 2005 (4 pages).

* cited by examiner

US 7,699,780 B2

FOCUSED ULTRASOUND SYSTEM WITH ADAPTIVE ANATOMICAL APERTURE SHAPING

FIELD OF INVENTION

The present invention relates generally to apparatus and methods for delivering acoustic energy, and more particularly to apparatus and methods for delivering diagnostic and/or therapeutic ultrasound energy from a transducer towards a target region of a subject.

BACKGROUND

Devices and systems using acoustic energy, particularly within the ultrasonic range, i.e., acoustic waves with a frequency greater than about twenty kilohertz (20 kHz), and more typically between fifty kiloHertz and ten MegaHertz (0.05-10 MHz), have been used to diagnose and treat patients. Ultrasonic energy may be employed to obtain images of a patient during a diagnostic or therapeutic procedure. In addition, ultrasound systems have been used for treating tissue, e.g., by directing acoustic energy towards a target tissue region within a patient, such as a cancerous or benign tumor, to coagulate, necrose, generate mechanical damage (by cavitation) or otherwise heat the tissue region. For example, one or more piezoelectric transducers may be disposed adjacent a patient's body and used to deliver high intensity acoustic waves, such as ultrasonic waves, at an internal tissue region of a patient to treat the tissue region. An exemplary focused ultrasound system is disclosed in U.S. Pat. No. 4,865,042 issued to Umemura et al. The acoustic energy emitted from such a system may be focused at a desired focal zone to deliver thermal energy to the target tissue region.

Focused ultrasound procedures may allow a patient to be treated while avoiding invasive surgery. For example, a focused ultrasound system that includes a single concave transducer has been used to treat breast, uterine and other tumors. Such transducer transmits an acoustic beam, which converges into a focus in target tissue to treat tissue. However, the acoustic beam may transverse through an organ, such as a breast nipple, or other sensitive areas, either before the beam converges into the focus (i.e., in a near field) or beyond the target tissue (i.e., in a far field). These areas have a high absorption coefficient compared to regular tissue, thereby risking damage to non targeted tissue at the near field and/or the far field. Also, in some cases, the acoustic beam may impinge on a tissue (e.g., bone tissue) that would not allow the beam to pass through by reflecting and/or absorbing most of the impinging energy. As a result, the acoustic beam may not reach the target tissue, and may generate undesired heating at the tissue surface that is blocking or interfering the acoustic beam. In some cases, the heating of bone tissue may also heat, and adversely affect, a nerve that is adjacent the bone tissue. A similar situation could happen with volumes in the body that are filled with air acting as total reflector for acoustic beam, thereby blocking the beam from propagating to the target tissue region.

A transducer can sometimes be positioned in a way so that the acoustic beam can reach target tissue, while reducing a risk of passing through tissues that have a high risk for damage. However, positioning the transducer in a way that will avoid tissue damage at tissue desired to be protected may complicate treatment planning and treatment procedure. Further, positioning the transducer to treat target tissue, while avoiding passage of the acoustic wave energy through tissue desired to be protected may not be practical or possible in some cases. For example, when treating a liver or a kidney, it may be necessary to deliver acoustic energy between the ribs. In such cases, moving the transducer away from the ribs, e.g., and positioning it below the ribs, may render the treatment ineffective.

SUMMARY OF THE INVENTION

In one embodiment of the invention, a method is provided for treating body tissue using an ultrasound transducer, the ultrasound transducer comprising a plurality of transducer elements, the method including directing the ultrasound transducer towards target body tissue; and delivering ultrasound energy from the transducer elements in an ultrasound energy path towards the target tissue such that an energy intensity at the target tissue is at or above a prescribed treatment level, while an energy intensity at tissue to be protected in the ultrasound energy delivery path outside of the target tissue is at or below a prescribed safety level.

In another embodiment, a focused ultrasound system includes an ultrasound transducer device having a plurality of transducer elements; drive circuitry coupled to the transducer elements; and a drive signal controller coupled to the drive circuitry. The drive signal controller is configured to control acoustic energy delivered from the transducer elements in an ultrasound energy path towards the target tissue such that an energy intensity at the target tissue is at or above a prescribed treatment level, while an energy intensity at tissue to be protected in the ultrasound energy delivery path outside of the target tissue is at or below a prescribed safety level.

In yet another embodiment, a method is provided for determining a treatment plan for treating a patient using a focused ultrasound system, the focused ultrasound system including a transducer having a plurality of transducer elements, the method including identifying target tissue to be treated; prescribing a treatment energy level for treating the target tissue by directing ultrasound energy from the transducer elements at the target tissue in an ultrasound energy path; identifying tissue to be protected in the ultrasound energy path outside of the target tissue; prescribing a safety energy level for protecting the tissue to be protected; and determining operational parameters for controlling the transducer elements to deliver ultrasound energy in the ultrasound energy path such that an energy intensity at the target tissue is at or above the prescribed treatment level, while an energy intensity at the tissue to be protected is at or below the prescribed safety level.

In still another embodiment, a method is provided for creating a treatment plan for treating a patient using a focused ultrasound system, the focused ultrasound system comprising a transducer having a plurality of transducer elements, the method including creating a model representing energies to be delivered by respective transducer elements of the transducer; calculating an energy density based on the model at a tissue region in an ultrasound energy path of the transducer elements, the tissue region associated with patient body tissue to be protected from ultrasound energy treatment; and determining whether the calculated energy density at the tissue region to be protected exceeds a prescribed safety threshold.

In yet another embodiment, a method is provided for creating a treatment plan for using a focused ultrasound system, the focused ultrasound system comprising a transducer having a plurality of transducer elements, the method comprising directing the ultrasound transducer towards a first region of a subject; delivering a diagnostic-level ultrasound energy from the transducer elements towards the first region; obtaining an energy density associated with the delivered ultrasound energy at a second region of the subject; determining whether the energy density at the second region exceeds a prescribed safety threshold; and reducing the delivered ultrasound energy from one or more of the transducer elements if the determined energy density at the second region is above the prescribed safety threshold.

Other aspects and features of embodiments of the invention will be evident from reading the following detailed description of the preferred embodiments, which are intended to illustrate, and not to limit, the invention.

BRIEF DESCRIPTION OF THE DRAWINGS

Various embodiments of the invention are described hereinafter with reference to the figures. It should be noted that the figures are not drawn to scale and elements of similar structures or functions are represented by like reference numerals throughout the figures. It should also be noted that the figures are only intended to facilitate the description of specific embodiments of the invention, and are not intended as an exhaustive description of, or as a limitation on, the scope of the invention. In addition, aspects or features described in conjunction with a particular embodiment of the invention are is not necessarily limited to that embodiment, and may be applicable in other embodiments.

DETAILED DESCRIPTION OF THE ILLUSTRATED EMBODIMENTS

Figure 1:
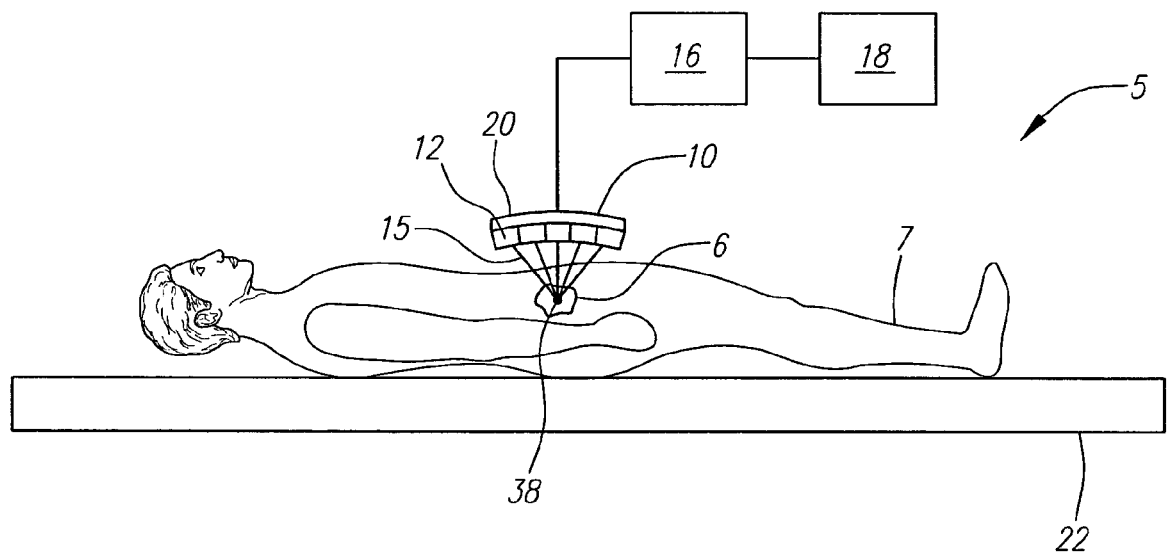
FIG. 1 illustrates an ultrasound system configured to deliver an acoustic treatment beam.

FIG. 1 illustrates a focused ultrasound system 5, which includes a transducer device 10, drive circuitry 16 coupled to the transducer device 10, and a controller 18 coupled to the drive circuitry 16. The transducer device 10 is configured to deliver acoustic energy (represented by beam 15) to target tissue 6 located inside a patient 7. The acoustic energy 15 may be used to coagulate, generate mechanical damage, necrose, heat, or otherwise treat the target tissue 6, which may be a benign or malignant tumor within an organ or other tissue structure (not shown). The transducer device 10 is coupled to a patient support 22 by a mechanical linkage (not shown), such as a positioner, for adjusting a position of the transducer device 10 relative to the patient support 22. Alternatively, the transducer device 10 can be coupled to a mechanical arm that is independent of the patient support 22.

In the illustrated embodiments, the transducer device 10 includes a structure 20 and a plurality of transducer elements 12 secured to the structure 20. The structure 20 is illustrated to have a curved shape. In other embodiments, the structure 20 can have other shapes, forms, and/or configurations so long as it provides a platform or area to which the transducer elements 12 can be secured. The structure 20 may be substantially rigid, semi-rigid, or substantially flexible, and can be made from a variety of materials, such as plastics, polymers, metals, and alloys. The structure 20 can be manufactured as a single unit, or alternatively, be assembled from a plurality of components that are parts of the transducer device 10. In some cases, the transducer device 10 can include a coupling membrane (not shown), such as an inflatable body or a balloon, for providing or improving an acoustic coupling between the transducer elements 12 and a skin of the patient 7, while focused ultrasound energy is being delivered. Electrodes and conducting wires (not shown) may also be provided in a known manner for coupling the transducer elements 12 to the driver 16. The electrodes for the transducer elements 12 are preferably housed within, and exit from, the structure 20 for coupling to the driver 16 and/or the controller 18.

The transducer elements 12 are coupled to the driver 16 and/or controller 18 for generating and/or controlling the acoustic energy emitted by the transducer elements 12. For example, the driver 16 may generate one or more electronic drive signals, which may be controlled by the controller 18. The transducer elements 12 convert the drive signals into acoustic energy 15, which may be focused using conventional methods. The controller 18 and/or driver 16 may be separate or integral components. It will be appreciated by those skilled in the art that the operations performed by the controller 18 and/or driver 16 may be performed by one or more controllers, processors, and/or other electronic components, including software and/or hardware components. The terms controller and control circuitry may be used herein interchangeably. Similarly, the terms driver and drive circuitry may be used herein interchangeably.

The driver 16, which may be an electrical oscillator, may generate drive signals in the ultrasound frequency spectrum, e.g., as low as fifty kilohertz (50 KHz), or as high as ten megahertz (10 MHz). Preferably, the driver 16 provides drive signals to the transducer elements 12 at radio frequencies (RF), for example, between about one hundred Kiloherz to ten Megahertz (0.1-10 MHz), and more preferably between 200 Kilohertz and three Megahertz (0.20 and 3.0 MHz), which corresponds to wavelengths of approximately 7.5 mm to 0.5 mm in tissue. However, in other embodiments, the driver 16 can be configured to operate in other frequency ranges. When the drive signals are provided to the transducer elements 12, the transducer elements 12 emit acoustic energy 15 from their respective exposed surfaces, as is well known to those skilled in the art.

The controller 18 may control the amplitude, and therefore the intensity or power of the acoustic waves transmitted by the transducer elements 12. The controller 18 may also control a phase component of the drive signals to respective transducer elements 12 of the transducer device 10, e.g., to control a shape or size of a focal zone 38 generated by the transducer elements 12 and/or to move the focal zone 38 to a desired location. For example, the controller 18 may control the phase shift of the drive signals to adjust a focal distance of the focal plane, i.e., the distance from the face of the transducer element 12 to the center of the focal zone.

In the illustrated embodiments, the controller 18 is also used to control respective transducer elements 12 to protect a tissue region, e.g., healthy tissue that is adjacent target tissue, at the far field relative to target tissue, or at the near field relative to target tissue, while treating the target tissue. Particularly, the controller 18 is configured to control an amplitude, a phase, or a combination of both, of respective transducer elements 12, such that an energy intensity at the target tissue is above a prescribed threshold (treatment threshold) level sufficient to treat the target tissue, while an energy intensity at tissue (sensitive tissue) desired to be protected is below a prescribed threshold (safety threshold) level for protection of the sensitive tissue. For example, the controller 18 can generate a drive signal to reduce an energy delivered to the sensitive tissue by, or otherwise not activate one of, the transducer elements 12, thereby creating a zone of relatively lower energy at the sensitive tissue. As used in this specification, the term, "sensitive tissue", refers to tissue that is desired to be protected from adverse affects caused by the ultrasound wave energy, and is not be limited to tissue having a certain sensitivity. Methods of creating a treatment plan that includes a No Pass Region (NPR—a region through which a beam does not pass) or a Limited Energy Density Region (LEDR—a region having limited energy density), and methods of performing a treatment procedure that involves creating NPR(s) and/or LEDR(s) are described in detail below.

As explained above, the transducer elements 12 convert the drive signals into acoustic energy, represented by energy beam 15. As the acoustic energy 15 passes through the patient's body, the acoustic energy 15 is absorbed in the tissue and converted to heat where the temperature rise depends on the energy density. In this manner, in the pass zone, the temperature rise is insignificant, while at the focal zone 38 within the target region, the temperature rise is significant, thereby raising the temperature of tissue within the target region. In accordance generally with embodiments of the invention, the acoustic energy 15 may be focused on the target region to raise the temperature of the tissue to coagulation, while minimizing damage to surrounding healthy tissue. Exemplary apparatus for measuring and/or calibrating the energy output of a transducer device are described in U.S. patent application Ser. No. 10/005,845, filed Dec. 3, 2001. The disclosure of this application and any references cited therein are expressly incorporated herein by reference.

In the illustrated embodiments, each of the transducer elements 12 may be a one-piece piezoceramic part, or alternatively, be composed of a mosaic arrangement of a plurality of small piezoceramic elements (e.g., a phased array). The piezoceramic parts or elements may have a variety of geometric shapes, such as hexagons, triangles, squares, and the like. The material used could be composite or piezoceramic or any other material that could transform electrical signal into acoustic wave.

The transducer elements 12 can be time-delayed or phase-delayed driven. Delay elements (not shown), are well known in the art, and may be coupled to respective transducer elements 12 for providing delay times for the respective transducer elements 12, such that the delivered acoustic waves by the transducer elements 12 focuses onto a zone. If the transducer elements 12 include a plurality of piezoceramic elements, each element may be coupled to a respective delay element. The delay elements may be implemented as a part of the ultrasound transducer device 10, the driver 16, or the controller 18.

In alternate embodiments, the transducer elements 12 can be movably secured to the structure 20 such that the position and/or shape of the focal zone 38 can be varied during use. In such cases, the transducer device 10 includes a positioner for moving the transducer elements 12. The positioner can, for example, include a motor, such as an electric motor or a piezoelectric motor, a hydraulic, or a gimbal system. In some embodiments, the structure 20 can include a plurality of movable sections to which one or more of the transducer elements 12 is secured. In such cases, the movable sections may be installed on respective gimbals, wherein the transducer elements 12 would be movable by operation of the gimbals. The transducer elements 12 can be configured to move in one or multiple degrees of freedom, e.g., with two to six degrees of freedom.

As described previously, the controller 18 is configured to deliver acoustic energy to target tissue, while protecting sensitive tissue (at NPR and/or LEDR). Such is accomplished by the controller 18 controlling the transducer elements 12 in accordance with a prescribed treatment plan. The treatment plan preferably includes one or more treatment sites represented by thermal dose properties, and one or more safety sites associated with tissue desired to be protected. The treatment plan preferably ensures complete ablation of target tissue 6 by planning a series of sonications that will apply a respective series of thermal doses at various locations within the target tissue 6, while ensuring that an acoustic energy beam does not intersect or otherwise damage a sensitive tissue region. For example, for certain sensitive tissue, the treatment plan can be configured to ensure that the acoustic energy beam will have limited intensity—i.e., below a user prescribed maximum allowable energy density, as it passes through the sensitive tissue region, thereby creating a LEDR, to prevent injury to tissue desired to be protected. On the other hand, for other sensitive tissue, the treatment plan can be configured to ensure that the acoustic energy beam does not pass through the sensitive tissue region, thereby creating a NPR—which can be considered a special case of LEDR with the user prescribed maximum allowable energy density being zero. In the illustrated embodiment, the treatment plan prescribes criteria for creating a beam having beam aperture region(s) of zero or limited density, as well as for control of the ultrasound element power and/or phase, to protect the sensitive tissue regions.

In order to construct the treatment plan, a planner can be provided. The planner can be implemented using a processor (not shown) to perform specific functions. The processor can be a component of the drive circuitry 16, a component of the controller 18, or a separate unit that is coupled to one or both of the drive circuitry 16 and the controller 18. In some cases, the processor is associated with a computer. The planner uses input from a user interface and an imager to create a treatment plan. For example, in one implementation, a user specifies the clinical application protocol depending on the body tissue region to be treated, i.e., breast, pelvis, eye, prostate, etc., via the user interface. Selection of the clinical application protocol may control at least some default thermal dose prediction properties, such as thermal dose threshold, thermal dose prediction algorithm, maximum allowed energy for each thermal dose, thermal dose duration for each treatment site, cooling time between thermal doses, and electrical properties for the transducer. In other implementations, some or all of these properties are input through the user interface, as user specified thermal dose prediction properties. Other properties that may be input as user specified thermal dose prediction properties are the sonication grid density, i.e., how much the sonications should overlap, and the operational parameters of the transducer elements 12. In some embodiments, a user may edit any of the default parameters via the user interface. In one implementation, the user interface comprises a Graphical User Interface (GUI), which allows a user to employ a mouse or a touch screen device to navigate through menus or choices as displayed on a display device in order to make the appropriate selections and supply the required information.

In some embodiments, to further aid the planner in constructing the treatment plan, an imager supplies image(s) of target tissue 6 that can be used to determine treatment parameters, such as volume, position, and distance from a skin surface. In an exemplary implementation, the imager is a Magnetic Resonance Imaging (MRN) device and, in one implementation, the images provided are three-dimensional images of the target tissue 6. Alternatively, other imaging modalities may be used, such as ultrasound, x-ray, fluoroscope, computed-tomography, or positron-emission tomography, to create an image of the target tissue 6. The image can be a film image or a digitized image.

Once the planner receives the input from the user interface and the image(s) from the imager, the planner preferably automatically constructs a treatment plan. In one implementation, the treatment plan is a three-dimensional treatment plan. Alternatively, the treatment plan can be a two-dimensional treatment plan. User interfaces and methods for creating a treatment plan to treat target tissue with ultrasound energy are described in U.S. Pat. No. 6,618,620, the entire disclosure of which is expressly incorporated by reference herein.

Figure 2:
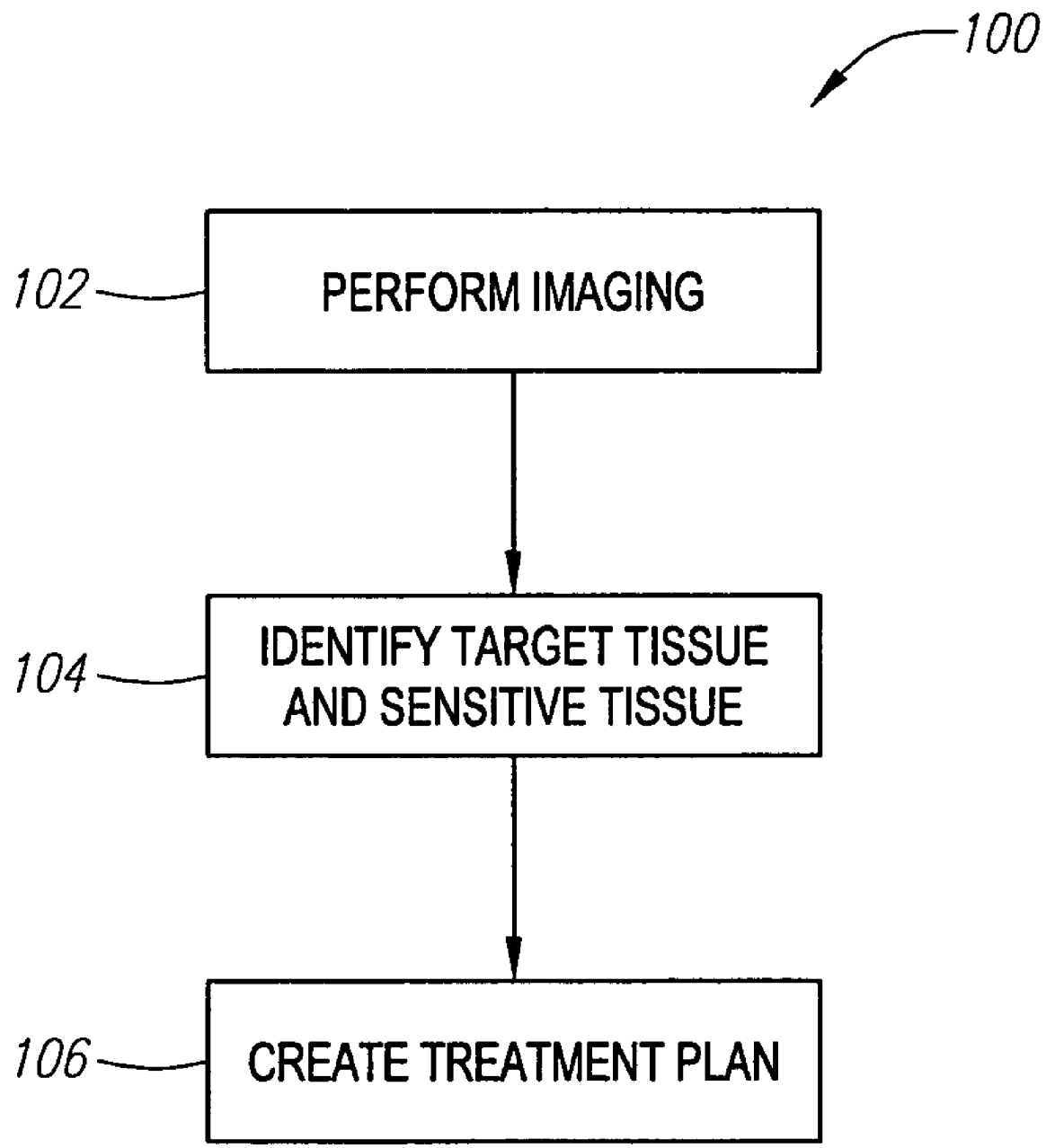
FIG. 2 illustrates a method of creating a treatment plan in accordance with some embodiments of the invention.
Figure 3A:
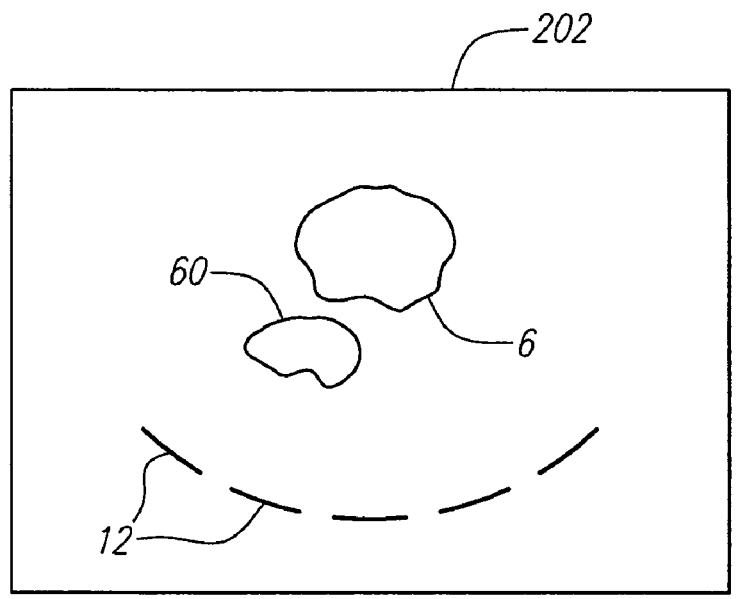
FIG. 3A illustrates an example of an image frame that includes an image of target tissue and an image of tissue desired to be protected.

FIG. 2 illustrates a process for creating a treatment plan in accordance with some embodiments of the invention. First, an image of the target tissue 6 and the sensitive tissue is obtained using the imager (Step 102). FIG. 3A illustrates an example of an image frame 202, which includes an image of the target tissue 6 and an image of the sensitive tissue 60. In some cases, if the transducer device 10 is located adjacent the patient 7 in its operable position while the image 202 is obtained, the image 202 can further include an image of the transducer elements 12. Although a two-dimensional image is shown, in other embodiments, the image can be a three-dimensional image. The three-dimensional image can be formed from a plurality of voxels, or formed from a plurality of two-dimensional images. It should be noted that the term, "image", as used herein, is not be limited to image that is displayed, and can include images that are not displayed, e.g., an image in data format.

Figure 3B:
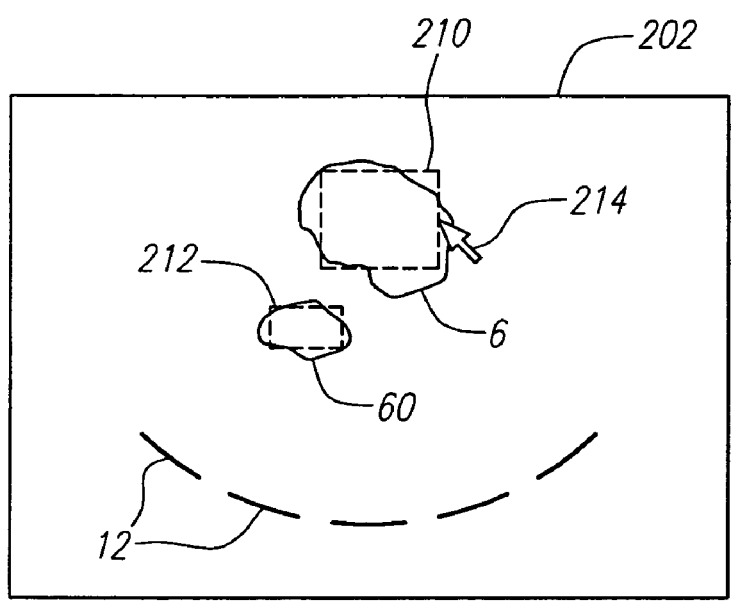
FIG. 3B illustrates frames being drawn in the image of FIG. 3A.

Next, the target tissue 6 and the sensitive tissue 60 are identified in the image frame 202 (Step 104). In the illustrated embodiment, the image can be digitized and be presented in a computer screen. In such cases, a physician can use the user interface to identify the target tissue 6 and the sensitive tissue 60 in the screen. For example, the physician can use a mouse to position a pointer 214 for drawing a frame (target frame) 210 around the target tissue 6 and a frame (safety frame) 212 around the sensitive tissue 60 (FIG. 3B). Although rectangular frames are illustrated in the example, in other embodiments, the target frame 210 and the safety frame 212 can each have other and differing shapes or profiles. In some cases, each of the target frame 210 and the safety frame 212 is a three-dimensional surface that encompasses the target tissue 6 and the sensitive tissue 60, respectively. In other embodiments, instead of creating frames around images of the target tissue 6 and the sensitive tissue 60, the physician can identify a point (target point) within the target tissue region and a point (sensitive point) within the sensitive tissue region.

Next, data, e.g., size, shape, position, associated with the identified target tissue 6 and the identified sensitive tissue 60 are passed to the planner, which performs calculations to create a treatment plan (Step 106). The treatment plan preferably includes operational parameter(s), e.g., phase, amplitude, etc., for each of the transducer elements 12, such that an energy intensity generated at the target tissue 6 is sufficiently high to adequately treat (i.e., heat) the target tissue 6, while an energy intensity generated at the sensitive tissue 60 is sufficiently low to protect the sensitive tissue 60 from thermal injury.

Figure 4:
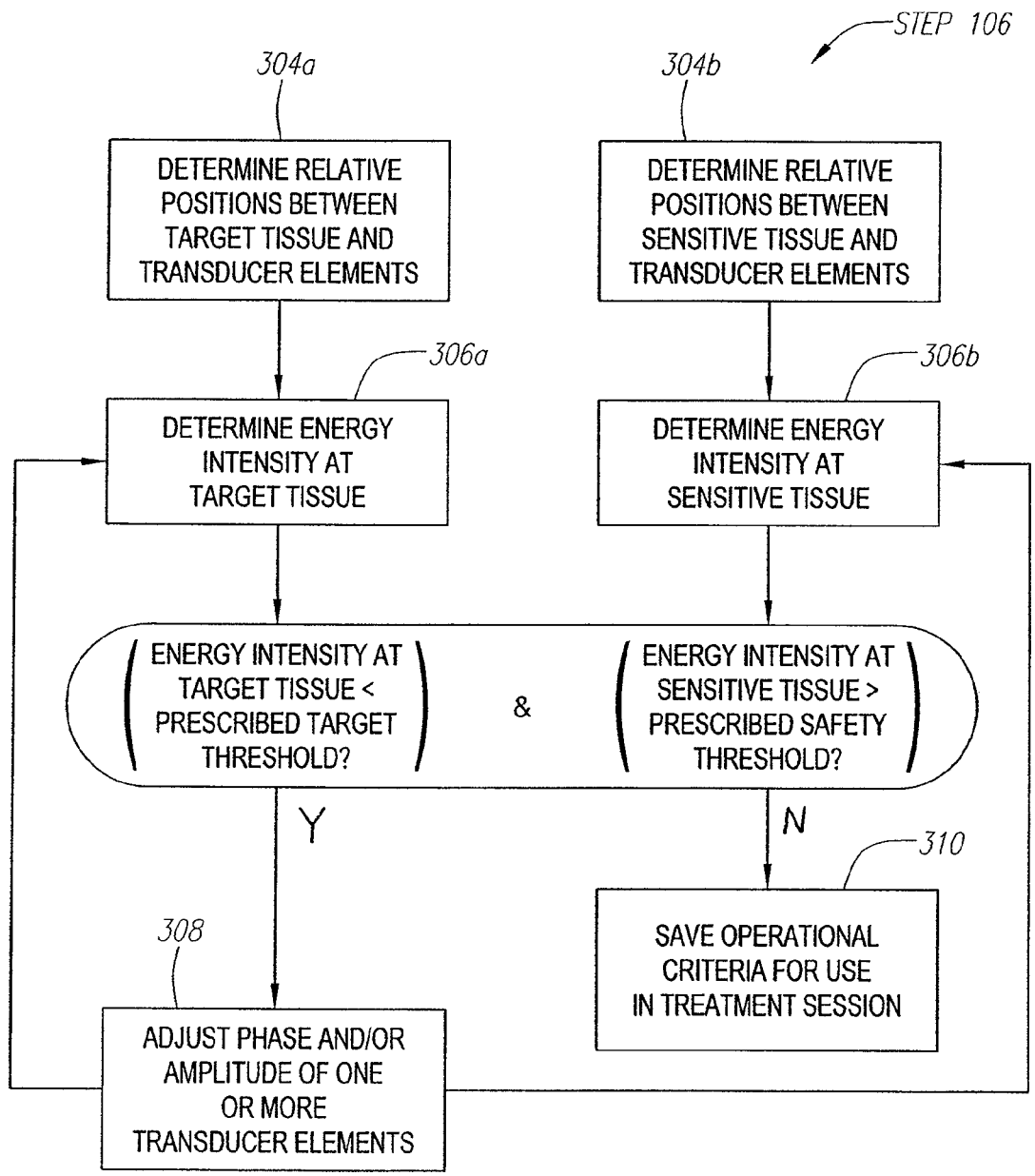
FIG. 4 illustrates a method of determining operational parameter(s) for use in a treatment procedure in accordance with some embodiments of the invention.

Various techniques can be employed to create the treatment plan. FIG. 4 illustrates an acoustic wave simulation technique to create the treatment plan in accordance with some embodiments of the invention. First, the relative positions between the target tissue 6 and the respective transducer elements 12, and the relative positions between the sensitive tissue 60 and the respective transducer elements 12, are determined (Steps 304a and 304b). For the purpose of determining the relative positions between the target tissue 6 and the respective transducer elements 12, the position of a point within the target frame 210 or the position of multiple target points can be used to represent the location of the target tissue 6. Similarly, the position of a point within the safety frame 212 or the position of multiple safety points can be used to represent the position of the sensitive tissue 6. In some embodiments, if the image frame 202 also includes images of the transducer elements 12, the image frame 202 can be used to determine the relative positions between the target tissue 6 and the respective transducer elements 12, and the relative positions between the sensitive tissue 60 and the respective transducer elements 12.

Next, based on the determined relative positions between the target tissue 6 and the respective transducer elements 12, and based on an assumption of the operational parameter(s) of each of the transducer elements 12, an energy intensity at the target tissue 6 can be determined (Step 306a). Similarly, based on the determined relative positions between the sensitive tissue 60 and the respective transducer elements 12, and based on the assumption of the operational parameter(s) of each of the transducer elements 12, an energy intensity at the sensitive tissue 60 can be determined (Step 306b). If the predicted temperature or the energy intensity at the target tissue 6 is below a prescribed treatment threshold, e.g., a minimum temperature that is required to treat the target tissue 6, then the phase, amplitude, or both of one or more of the transducer elements 12 can be adjusted, and the step of calculating the temperature or energy intensity at the target tissue 6 is repeated until the temperature at the target tissue 6 is above the prescribed treatment threshold (Step 308).

If the energy intensity at the sensitive tissue 60 is above a prescribed safety threshold, e.g., a maximum energy level above which the sensitive tissue 60 will be injured, then the phase, amplitude, or both of one or more of the transducer elements 12 can be adjusted, and the step of calculating the energy intensity at the sensitive tissue 60 is repeated until the energy intensity at the sensitive tissue 60 is below the prescribed safety threshold (Step 308). In some cases, the energy contribution from one or more of the transducer elements 12 can be assumed to be zero in the calculation, which represents the scenario in which the corresponding transducer element(s) 12 will not be activated by the controller 18 during an execution of the treatment plan. In other embodiments, besides achieving desired temperature or energy intensities at the target tissue 6 and the sensitive tissue 60, operational parameter(s) can also be adjusted to vary a size, shape, and/or location of the beam aperture to protect tissue having a certain size and shape. In still further embodiments, result of the above calculation is automatically optimized using physiological parameters, such as perfusion, diffusion, specific heat, heat conductivity and absorption.

The step 308 of adjusting the operational parameter(s) of the transducer element(s) 12 is repeated until the temperature or energy intensity at the target tissue 6 is above the prescribed threshold, and the temperature or energy intensity at the sensitive tissue 60 is below the prescribed threshold. In some cases, a ray-model can be used to assist a physician to determine how to adjust the operation criteria of the transducer element(s) 12.

Figure 5A:
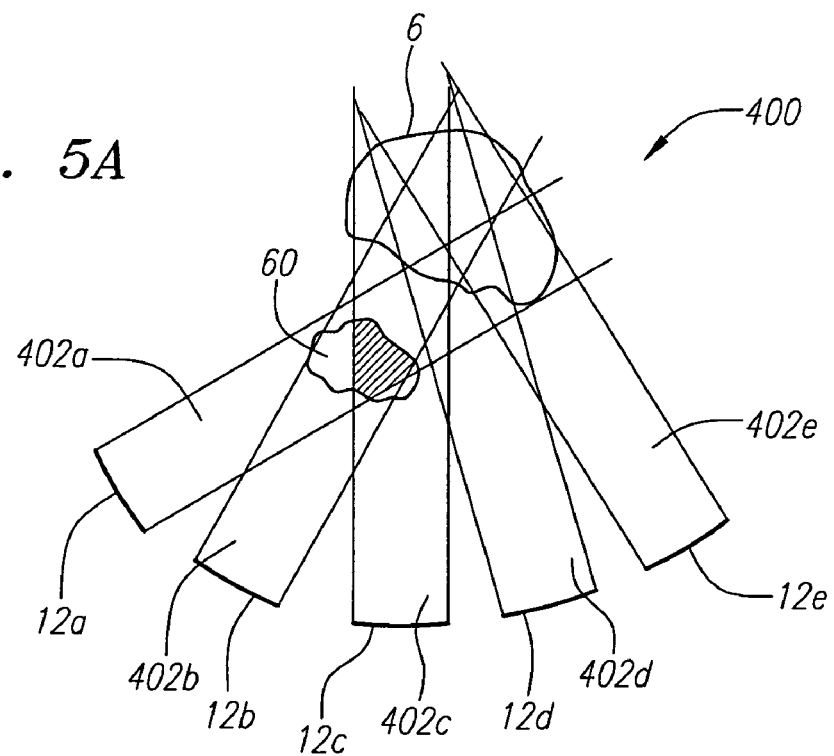
FIG. 5A illustrates an example of a ray-model.
Figure 5B:
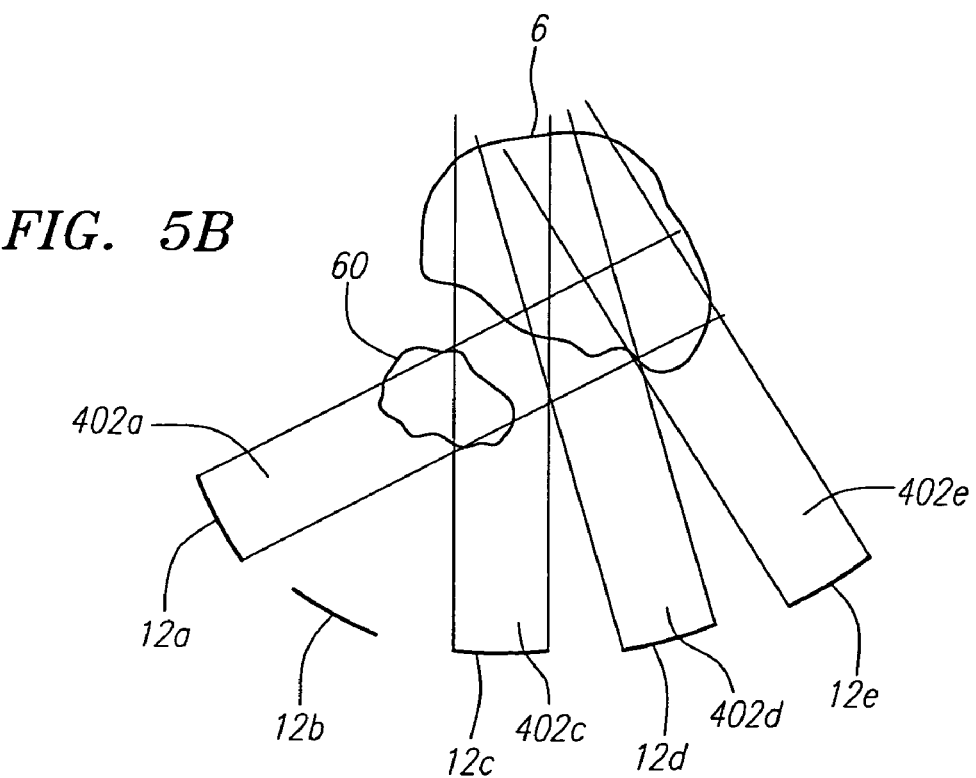
FIG. 5B illustrates the ray-model of FIG. 5A, with one of the rays being eliminated.

FIG. 5A illustrates an example of a ray-model 400. The ray-model 400 includes rays 402a-e extending from the surfaces of the respective transducer elements 12a-e, wherein each of the rays 402 has an angular emission dispersion that is associated with its corresponding wavelength and its geometry. For any of the transducer elements 12 which has a main lobe of a ray 402 that intersects the sensitive tissue 60, the operational parameter(s) for that transducer element 12 can be adjusted to reduce or eliminate the corresponding energy intensity. As shown in the example, rays 402a-c intersect the sensitive tissue 60. To reduce the energy intensity at the sensitive tissue 60, the ray 402b is eliminated, i.e., transducer element 12b is not activated during the treatment procedure (FIG. 5B). Although the ray model 400 is illustrated in graphical form, in other embodiments, the ray model 400 can be a mathematical model that is not graphically displayed. It should be noted that other techniques can also be used to determine how to adjust the operation criteria for the transducer elements 12. For example, instead of using the ray-model, other models or a trial-and-error technique can be used in alternative embodiments.

After the operational parameter(s) for the transducer elements 12 has been determined, the operational parameter(s) can then be saved as a part of the treatment plan in a memory for use to treat the patient 7 (Step 310). The memory can be electronically coupled to the controller 18, internal to the controller 18, or separate from the controller 18. An exemplary method of using the operational parameter(s) to treat the patient 7 is described below.

In other embodiments, instead of performing acoustic wave simulations to create the treatment plan, the focused ultrasound system 5 itself can be used to create the treatment plan. In such cases, the transducer elements 12 can be configured to emit acoustic wave energy at low (or sub-lethal) intensity (e.g., at an energy level that does not harm tissue) towards the target tissue 6. Next, the temperatures or energy intensities or other tissue parameters $E1_p$ and $E2_p$ at the respective target tissue 6 and the sensitive tissue 60 are measured. In some embodiments, this step comprises capturing a temperature sensitive image (temperature map) of the target tissue 6 and the sensitive tissue 60. The temperature sensitive image will illustrate the actual thermal dose distribution resulting from the application of the acoustic wave energy. In the illustrated embodiments, a ratio $R_T$ between a desired treatment energy intensity $E1_t$ at the target tissue 6 and $E1_p$ is calculated (i.e., $R_T = E1_t/E1_p$), and the ratio $R_T$ is used to multiply the $E2_p$ to obtain a predicted treatment energy intensity $E2_t$ at the sensitive tissue 60 ($E2_t = R_T \times E2_p$). In such case, if $E2_t$ exceed a prescribed threshold, the operational parameter(s) of the transducer element(s) are adjusted until $E2_t$ is below the prescribed threshold. In other embodiments, instead of calculating the ratio $R_T$, the measured energy intensities $E1_p$ and $E2_p$ are compared (e.g., by use of a processor) based on measured temperatures or with respective prescribed treatment threshold and safety threshold. If $E1_p$ is below the adjusted treatment threshold, or if $E2_p$ is above the adjusted safety threshold, the operational parameter(s) of the transducer element(s) 12 are then adjusted, until a desired temperature or energy intensity at the target tissue 6 and a desired energy intensity at the sensitive tissue 60 are obtained. The final determined operational parameter(s) of each of the transducer elements 12 are then saved in a memory so that they can then be used in a treatment session to treat the patient 7.

It should be noted that the methods of creating the treatment plan are not limited to the examples described previously, and that other methods can be used in alternative embodiments of the invention. By way of non-limiting example, instead of, or in addition to, phase and amplitude parameters, the treatment plan can include other operational parameter(s), such as frequency, duration, sonication power, and the position and mode of the focal spot for each treatment site. Embodiments of the above described method can include the step(s) of adjusting any one or a combination of the above and/or other operational parameters. If one or more of the transducer elements 12 are configured to move relative to the structure 20, the treatment plan could further include the step of adjusting a position of one or more transducer elements 12. Once the treatment plan has been determined, it is presented in a relevant format to the controller to allow the controller 18 to undertake treatment of the patient 7. If the controller 18 itself is implemented to perform the functions of the planner, then the step of passing the treatment plan to the controller is obviously not necessary.

When treating the patient 7 using the system 5, the transducer device 10 is first positioned relative to the patient 7. Particularly, the relative position between the transducer device 10 and the patient 7 should be substantially the same as that associated with the treatment planning session. In some cases, if the treatment session immediately follows the treatment planning session, the relative position between the transducer device 10 and patient 7 would remain the same, and the positioning of the transducer device 10 is not necessary.

Once the treatment plan is determined and the transducer device 10 is properly positioned relative to the patient 7, the transducer device 10 delivers focused ultrasound energy to the target tissue 6 in accordance with the treatment plan. Particularly, the driver 16 and/or the controller 18 are used to generate and/or to control the acoustic energy emitted by the transducer device 10 based on the operational parameter(s) prescribed by the treatment plan. For example, the driver 16 and/or the controller 18 can control a phase and/or an amplitude of one or more of the transducer elements 12, such that the phase and the amplitude of each of the transducer elements 12 correspond to those determined in the treatment plan. As a result, the energy intensity at the target tissue 6 is sufficiently high to coagulate, necrose, heat, or otherwise treat the target tissue 6. Because the treatment plan is designed to create a low energy region or no energy pass zone at the sensitive tissue 60, during the treatment session, the energy intensity at the sensitive tissue 60 is below a prescribed threshold, which, for example, could be defined as "no energy," thereby protecting the sensitive tissue 60 from being injured by acoustic energy.

In some embodiments, if the transducer elements 12 are configured to move relative to the structure 20, the driver 16 and/or the controller 18 can be used to control positions of the transducer element(s) 12 in accordance with that prescribed by the treatment plan to thereby adjust the position, shape, and/or size of the focal zone 38. After the desired treatment effect was achieved, the patient 7 is then removed from the transducer device 10, or vice versa.

By means of non-limiting example, the above described method and apparatus can be used to treat the liver. When treating liver through ribs, a transducer having a plurality of transducer elements, can be placed as close as possible to the ribs (e.g., approximately 1 cm or less). In such case, the driver 16 and/or the controller 18 can be configured to turn off transducer elements directed at ribs, while activating transducer elements that are directed between ribs.

Although the above examples have been described with reference to creating one beam aperture for protecting one sensitive tissue 60, in other embodiments, the same or similar methods can also be used to create a beam aperture or a plurality of beam apertures for protecting more than one sensitive tissue 60. Similarly, in other embodiments, the same or similar methods can be used to create a plurality of focal zones 38, thereby allowing treatment of multiple target regions simultaneously.

Although particular embodiments of the invention have been shown and described, it should be understood that the above discussion is not intended to limit the invention to these illustrated and described embodiments.

What is claimed:

1. A focused ultrasound system, comprising:
an ultrasound transducer device having a plurality of transducer elements;
drive circuitry coupled to the transducer elements; and
a drive signal controller coupled to the drive circuitry, the drive signal controller configured to individually control delivery of acoustic energy from the transducer elements along an ultrasound energy path towards the target tissue such that an energy intensity measured at the target tissue remains at or above a prescribed treatment level, while an energy intensity measured at tissue to be protected in the ultrasound energy delivery path and outside of the target tissue remains at or below a prescribed safety level, wherein the drive signal controller controls one or more of the transducer elements to create a limited energy density at the tissue to be protected in the ultrasound energy path.

2. The system of claim 1, wherein one or both of the prescribed treatment level and prescribed safety level comprise a temperature threshold or a thermal dose threshold.

3. The system of claim 1, wherein the drive signal controller controls one or more of the transducer elements to provide a beam aperture having a size and a shape for protecting the tissue to be protected in the ultrasound energy path.

4. The system of claim 1, wherein the drive signal controller does not activate or deactivates one or more of the transducer elements for protecting the tissue to be protected in the ultrasound energy path while delivering ultrasound energy to the focal volume.

5. The system of claim 1, wherein the drive signal controller causes one or more of the transducer elements to deliver acoustic energy at an energy level that is lower than an acoustic energy level delivered by one or more other of the transducer elements for protecting the tissue to be protected in the ultrasound energy path while delivering ultrasound energy.

6. A method for creating a treatment plan for treating a patient using a focused ultrasound system, the focused ultrasound system comprising a transducer having a plurality of transducer elements, the method comprising:
identifying target tissue to be treated;
identifying tissue to be protected along an ultrasound energy path outside of the target tissue;
estimating energy intensities at the target tissue and the tissue to be protected based at least in part on the relative position between the transducer and the target tissue and the relative position between the transducer and the tissue to be protected;
specifying operational parameters of one or more of the transducer elements to cause the energy intensity delivered to the target tissue to remain above a prescribed treatment threshold while the estimated energy at the tissue to be protected remains below a prescribed safety threshold; and
creating a treatment plan based on the adjusted operational parameters.

7. The method of claim 6, wherein the identifying steps comprise: obtaining an image of tissue in the ultrasound energy path; and identifying the target tissue and the tissue to be protected in the image.

8. The method of claim 6, wherein the operational parameters are selected from the group consisting of a phase, an amplitude, a frequency, a power, and a duration of one or more of the transducer elements.

9. A method for treating a patient using a focused ultrasound system, the focused ultrasound system comprising a transducer having a plurality of transducer elements, the method comprising:
identifying target tissue to be treated;
identifying tissue to be protected along an ultrasound energy path outside of the target tissue;
emitting an acoustic wave towards the target tissue;
measuring energy intensities at the target tissue and the tissue to be protected; and
adjusting operational parameters of one or more of the transducer elements directed to the tissue to be protected if the measured energy intensity at the tissue to be protected is above a prescribed safety threshold while maintaining a minimum energy intensity at the target tissue.

10. A method for creating a treatment plan for treating a patient using a focused ultrasound system, the focused ultrasound system comprising a transducer having a plurality of transducer elements, the method comprising:
creating a model representing energies to be delivered to a patient by respective transducer elements of the transducer;
calculating an energy density based on the model at a tissue region along an ultrasound energy path of the transducer elements, the tissue region associated with patient body tissue to be protected from ultrasound energy treatment;
determining whether the calculated energy density at the tissue region to be protected exceeds a prescribed safety threshold;
determining adjustments to operational parameters of one or more of the transducer elements such that the energy density at the tissue region to be protected remains at or below the prescribed safety threshold while maintaining a minimum energy intensity at a target tissue; and
creating a treatment plan based on the model and the adjustments.

11. The method of claim 10, wherein the model comprises a plurality of rays extending from respective representations of surfaces of the respective transducer elements.

12. The method of claim 11, wherein the rays are created at respective resolutions that are comparable to wavelengths of energies output by the respective transducer elements.

13. The method of claim 10, wherein the adjusting comprises reducing one or more respective transducer element energies.

14. The method of claim 10, wherein the prescribed safety threshold comprises a thermal dose threshold or a temperature threshold.

15. The method of claim 10, wherein the prescribed safety threshold comprises a tissue parameter value.

16. A method using a focused ultrasound system, the focused ultrasound system comprising a transducer having a plurality of transducer elements, the method comprising:
directing the ultrasound transducer towards a first region of a subject;
delivering a sub-lethal ultrasound energy from the transducer elements towards the first region;
obtaining an energy density associated with the delivered ultrasound energy at a second region of the subject;
determining whether the energy density at the second region exceeds a prescribed safety threshold; and
reducing the delivered ultrasound energy from one or more of the transducer elements if the determined energy density at the second region is above the prescribed safety threshold while maintaining a minimum energy intensity at the first region.

17. The method of claim 16, wherein the subject comprises a body of a patient.

18. The method of claim 17, wherein the first region comprises a region of target tissue, and the second region comprises a region of tissue to be protected in an ultrasound energy path of the transducer elements outside of the target tissue region.

19. The method of claim 16, wherein the energy density at the second region is determined by obtaining a temperature or a thermal dose at the second region.

20. The method of claim 16 wherein the energy density at the second region is determined by obtaining a measurement of a tissue parameter related to tissue viability at the second region.

21. The method of claim 16, wherein the delivered ultrasound energy is reduced by changing a phase, an amplitude, or both, of a drive signal of the one of the transducer elements.

22. The method of claim 16, wherein the delivered ultrasound energy is reduced by not activating one of the transducer elements.

* * * * *